(12) United States Patent
Gangjee

(10) Patent No.: US 11,572,363 B2
(45) Date of Patent: *Feb. 7, 2023

(54) SUBSTITUTED BICYCLIC PYRIMIDINE COMPOUNDS WITH TUBULIN AND MULTIPLE RECEPTOR INHIBITION

(71) Applicant: Duquesne University of the Holy Spirit, Pittsburgh, PA (US)

(72) Inventor: Aleem Gangjee, Allison Park, PA (US)

(73) Assignee: Duquesne University of The Holy Spirit, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/130,395

(22) Filed: Dec. 22, 2020

(65) Prior Publication Data

US 2021/0188858 A1 Jun. 24, 2021

Related U.S. Application Data

(62) Division of application No. 16/437,257, filed on Jun. 11, 2019, now Pat. No. 10,906,910, which is a division of application No. 14/678,206, filed on Apr. 3, 2015, now Pat. No. 10,358,450.

(60) Provisional application No. 61/975,089, filed on Apr. 4, 2014.

(51) Int. Cl.
*C07D 487/04* (2006.01)
*A61P 35/00* (2006.01)
*A61P 35/02* (2006.01)
*A61K 31/519* (2006.01)

(52) U.S. Cl.
CPC .......... *C07D 487/04* (2013.01); *A61P 35/00* (2018.01); *A61P 35/02* (2018.01)

(58) Field of Classification Search
CPC .................... C07D 487/04; A61K 31/519
See application file for complete search history.

(56) References Cited

U.S. PATENT DOCUMENTS

| 2010/0010016 | A1 | 1/2010 | Gangjee |
| 2012/0264768 | A1 | 10/2012 | Gangjee |

FOREIGN PATENT DOCUMENTS

| WO | 2012106522 A2 | 8/2012 | |
| WO | WO-2015153955 A1 * | 10/2015 | .............. A61P 35/00 |

OTHER PUBLICATIONS

Gangjee et al., Discovery of Antitubulin Agents with Antiangiogenic Activity as Single Entities with Multitarget Chemotherapy Potential, ACS Med. Chem. Lett. 2014, vol. 5 480-484.
International Search Report and Written Opinion for PCT/US2015/024216 dated Jun. 15, 2015.
Extended European Search Report for 15773702.4-1452/3125899 PCT/US2015024216, dated Jun. 11, 2017, 9 pages.
Japanese Official Action for JP2016-559902 filed Sep. 22, 2016, dated Oct. 16, 2018.
European Official Communication for EP 15773702.4-1110 filed Sep. 22, 2016, dated Aug. 14, 2018.
Kerns, Edward et al., Drug-like Properties: Concepts, Structure Design and Methods: from ADME to Toxicity Optimization, (Elsevier, 2008) pp. 92-93.
Goosen et al., Pharmaceutical Research vol. 19, No. 1, 13-19 (Jan. 2002).
Fourie, International Journal of Pharmaceutics vol. 279, Issues 1-2, Jul. 26, 2004, pp. 59-66.
Edwards, J. Med. Chem 39 (1996), pp. 1112-1124.
Rautio, Eur. J. Pharm. Sci. 11, pp. 157-163 (2000).

* cited by examiner

*Primary Examiner* — Susanna Moore
(74) *Attorney, Agent, or Firm* — Buchanan Ingersoll & Rooney PC; Craig G. Cochenour, Esq.

(57) ABSTRACT

This invention provides substituted bicyclic pyrimidine compounds of the following formula:

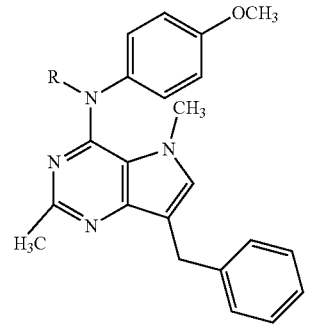

or a pharmaceutically acceptable salt thereof, wherein R is selected from the group consisting of a straight or a branched chain alkyl group having from 1 to 10 carbon atoms, wherein the alkyl group is partially or completely saturated. Methods of treating a patient diagnosed with cancer are disclosed comprising administering to the patient a therapeutically effective amount of the substituted bicyclic pyrimidine compounds, or a pharmaceutically acceptable salt thereof.

3 Claims, 5 Drawing Sheets

| Also identified as | Compound number |
|---|---|
| RP/AG/159-306 | 2 |
| RP/AG/159-313 | 3 |
| RP/AG/159-321 | 4 |
| RP/AG/159-341 | 5 |

SUBSTITUTED BICYCLIC PYRIMIDINE COMPOUNDS WITH TUBULIN AND MULTIPLE RECEPTOR INHIBITION

CROSS-REFERENCE TO RELATED APPLICATION

This utility patent application claims the benefit of co-pending U.S. patent application Ser. No. 16/437,257, filed Jun. 11, 2019, which is a divisional patent application of and claims priority to U.S. patent application Ser. No. 14/678,206, filed Apr. 3, 2015, now U.S. Pat. No. 10,358,450, granted Jul. 23, 2019, which claims priority to U.S. Provisional Patent Application Ser. No. 61/975,089, filed on Apr. 4, 2014. The entire contents of U.S. patent application Ser. Nos. 16/437,257 and 14/678,206, and U.S. Provisional Patent Application Ser. No. 61/975,089, are incorporated by reference into this utility patent application as if fully written herein.

STATEMENT REGARDING FEDERALLY SPONSORED RESEARCH OR DEVELOPMENT

This invention was made with government support under Grant No. CA136944 awarded by the National Institute of Health, National Cancer Center. The government has certain rights in this invention.

FIELD OF THE INVENTION

This invention provides for the design and preclinical evaluation of substituted bicyclic pyrimidine compounds (as single agents) having tubulin and multiple receptor tyrosine kinase inhibition.

BACKGROUND OF THE INVENTION

1. Field of the Invention

The substituted bicyclic pyrimidine compounds of the present invention are single agents that have both cytotoxic and antiangiogenic effects. The antiangiogenic effect is mediated via inhibition of vascular endothelial growth factor-2 (VEGFR2). The cytotoxic effect is mediated by tubulin inhibition. The compounds, pharmaceutical compositions comprising the compounds, or their salts, solvates, and hydrates thereof, overcome two clinically important tumor resistance mechanisms that limit the activity of microtubule targeting agents: expression of P-glycoprotein and βIII tubulin.

2. Description of the Background Art

Agents that interfere with microtubules are important antitumor agents. Tumor angiogenic mechanisms that are vital for tumor growth and metastasis are targeted by antiangiogenic agents. Antiangiogenic agents are usually not tumoricidal but are mainly cytostatic. Combination chemotherapy with antiangiogenic and cytotoxic agents have shown significant promise and several studies with such combinations are in progress in the clinic.

SUMMARY OF THE INVENTION

This invention provides substituted bicyclic pyrimidine compounds and pharmaceutical composition comprising these compounds and salts, solvates and hydrates of these compounds. The compounds of this invention may act as single agents with both antiangiogenic and cytotoxic activities. The compounds of this invention have the advantages of circumventing the pharmacokinetic problems associated with delivery of multiple agents, of avoiding drug-drug interactions, of alleviating toxicity, and of delaying or preventing tumor cell resistance.

The present invention provides a compound comprising the following formula:

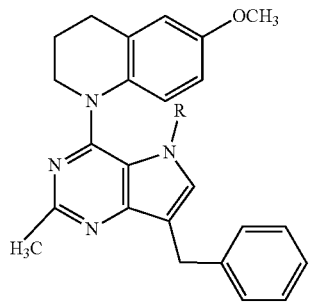

wherein R is selected from the group consisting of H and a straight or branched chain alkyl group having from 1 to 10 carbon atoms, wherein the alkyl group is partially or completely saturated. Another embodiment of this invention provides a pharmaceutical composition comprising this compound and pharmaceutically acceptable salts, hydrates, and solvates thereof.

Another embodiment of this invention provides a compound comprising the following formula:

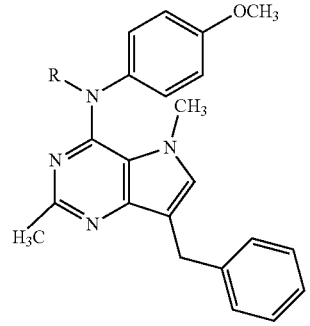

wherein R is selected from the group consisting of H and a straight or branched chain alkyl group having from 1 to 10 carbon atoms, wherein the alkyl group is partially or completely saturated. Another embodiment of this invention provides a pharmaceutical composition comprising this compound and pharmaceutically acceptable salts, hydrates, and solvates thereof.

In yet another embodiment of this invention, the following compounds are provided consisting of the group selected of 7-Benzyl-2-methyl-3H-pyrrolo[3,2-d]pyrimidin-4(5H)-one, 7-Benzyl-4-chloro-2-methyl-5H-pyrrolo[3,2-d]pyrimidine, 7-Benzyl-4-chloro-2,5-dimethyl-5H-pyrrolo[3,2-d]pyrimidine, 1-(7-Benzyl-2-methyl-5H-pyrrolo[3,2-d]pyrimidin-4-yl)-6-methoxy-1,2,3,4-tetrahydroquinoline, 7-Benzyl-N-(4-methoxyphenyl)-2,5-dimethyl-5H-pyrrolo[3,2-d]pyrimidin-4-amine, 7-Benzyl-N-(4-methoxyphenyl)-N,2,5-trimethyl-5H-pyrrolo[3,2-d]pyrimidin-4-amine, and 1-(7-Benzyl-2,5-dimethyl-5H-pyrrolo[3,2-d]pyrimidin-4-yl)-6-methoxy-1,2,3,4-tetrahydroquinoline, and pharmaceutical compositions of these compounds comprising pharmaceutically acceptable salts, hydrates, and solvates thereof.

Another embodiment of this invention provides a method of treating a patient diagnosed with cancer comprising administering to the patient a therapeutically effective amount of a compound described herein, or optionally pharmaceutical compositions comprising a therapeutically effective amount of these compounds as described herein and pharmaceutically acceptable salts, hydrates, and solvates thereof.

DESCRIPTION OF THE PREFERRED EMBODIMENTS

Figure 1:
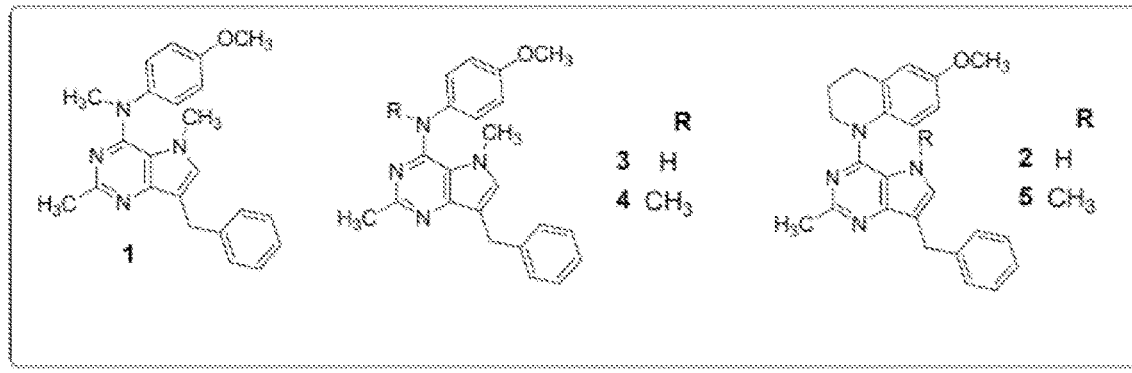
FIG. 1 shows compounds that are preferred embodiments of this invention.

As used herein, the term "patient" means members of the animal kingdom, including, but not limited to, human beings.

As used herein, the term "having cancer" means that the patient has been diagnosed with cancer. As used herein, the term "therapeutically effective amount" refers to that amount of any of the present compounds, or a pharmaceutical composition comprising any one or more of the compounds, or pharmaceutically acceptable salts, hydrates, or solvates thereof, required to bring about a desired effect in a patient. The desired effect will vary depending on the illness being treated. For example, the desired effect may be reducing tumor size, destroying cancerous cells, and/or preventing metastasis, any one of which may be the desired therapeutic response. On its most basic level, a therapeutically effective amount is that amount needed to inhibit the mitosis of a cancerous cell or to facilitate the reversal of multidrug resistance, particularly, for example due to P-glycoprotein (i.e. an effective mitotic inhibitory amount) or βIII tubulin. Any amount of mitotic inhibition or reversal of multidrug resistance will yield a benefit to a patient and is therefore within the scope of the invention.

The present invention provides a compound comprising the following formula:

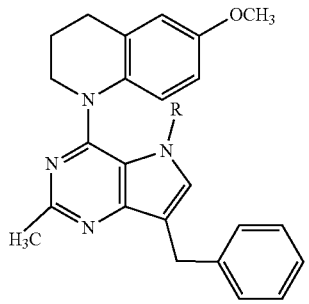

wherein R is selected from the group consisting of H and a straight or branched chain alkyl group having from 1 to 10 carbon atoms, wherein the alkyl group is partially or completely saturated. Another embodiment of this invention provides a pharmaceutical composition comprising this compound and pharmaceutically acceptable salts, hydrates, and solvates thereof.

Another embodiment of this invention provides a compound comprising the following formula:

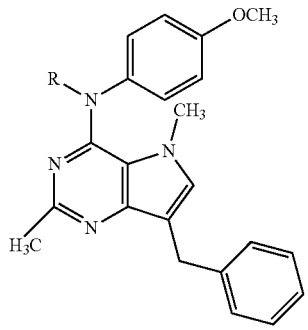

wherein R is selected from the group consisting of H and a straight or branched chain alkyl group having from 1 to 10 carbon atoms, wherein the alkyl group is partially or completely saturated. Another embodiment of this invention provides a pharmaceutical composition comprising this compound and pharmaceutically acceptable salts, hydrates, and solvates thereof.

In yet another embodiment of this invention, the following compounds are provided consisting of the group selected of 7-Benzyl-2-methyl-3H-pyrrolo[3,2-d]pyrimidin-4(5H)-one, 7-Benzyl-4-chloro-2-methyl-5H-pyrrolo[3,2-d]pyrimidine, 7-Benzyl-4-chloro-2,5-dimethyl-5H-pyrrolo[3,2-d]pyrimidine, 1-(7-Benzyl-2-methyl-5H-pyrrolo[3,2-d]pyrimidin-4-yl)-6-methoxy-1,2,3,4-tetrahydroquinoline, 7-Benzyl-N-(4-methoxyphenyl)-2,5-dimethyl-5H-pyrrolo[3,2-d]pyrimidin-4-amine, 7-Benzyl-N-(4-methoxyphenyl)-N,2,5-trimethyl-5H-pyrrolo[3,2-d]pyrimidin-4-amine, and 1-(7-Benzyl-2,5-dimethyl-5H-pyrrolo[3,2-d]pyrimidin-4-yl)-6-methoxy-1,2,3,4-tetrahydroquinoline, and pharmaceutical compositions of these compounds comprising pharmaceutically acceptable salts, hydrates, and solvates thereof.

Another embodiment of this invention provides a method of treating a patient diagnosed with cancer comprising administering to the patient a therapeutically effective amount of a compound having the formula:

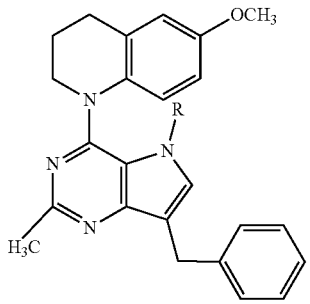

wherein R is selected from the group consisting of H and a straight or branched chain alkyl group having from 1 to 10 carbon atoms, wherein the alkyl group is partially or completely saturated, or optionally administering a therapeutically effective amount of said compound comprising pharmaceutically acceptable salts, hydrates, and solvates thereof, for treating the patient diagnosed with cancer.

Another embodiment of this invention provides a method of treating a patient diagnosed with cancer comprising administering to the patient a therapeutically effective amount of a compound having the formula:

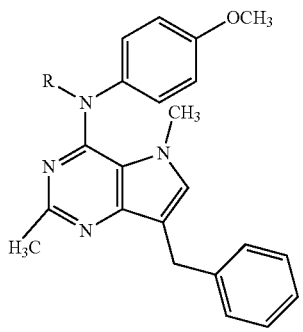

wherein R is selected from the group consisting of H and a straight or branched chain alkyl group having from 1 to 10 carbon atoms, wherein the alkyl group is partially or completely saturated, or optionally administering a therapeutically effective amount of said compound comprising pharmaceutically acceptable salts, hydrates, and solvates thereof, for treating the patient diagnosed with cancer.

Another embodiment of this invention provides a method of treating a patient diagnosed with cancer comprising administering to the patient a therapeutically effective amount of a compound selected from the group of 7-Benzyl-2-methyl-3H-pyrrolo[3,2-d]pyrimidin-4(5H)-one, 7-Benzyl-4-chloro-2-methyl-5H-pyrrolo[3,2-d]pyrimidine, 7-Benzyl-4-chloro-2,5-dimethyl-5H-pyrrolo[3,2-d]pyrimidine, 1-(7-Benzyl-2-methyl-5H-pyrrolo[3,2-d]pyrimidin-4-yl)-6-methoxy-1,2,3,4-tetrahydroquinoline, 7-Benzyl-N-(4-methoxyphenyl)-2,5-dimethyl-5H-pyrrolo[3,2-d]pyrimidin-4-amine, 7-Benzyl-N-(4-methoxyphenyl)-N,2,5-trimethyl-5H-pyrrolo[3,2-d]pyrimidin-4-amine, and 1-(7-Benzyl-2,5-dimethyl-5H-pyrrolo[3,2-d]pyrimidin-4-yl)-6-methoxy-1,2,3,4-tetrahydroquinoline, or optionally administering a therapeutically effective amount of said compound comprising pharmaceutically acceptable salts, hydrates, and solvates thereof, for treating the patient diagnosed with cancer.

This invention provides single agents, for example but not limited to, Compounds 1-5 of FIG. 1 that were designed to have both cytotoxic and antiangiogenic effects. The antiangiogenic effect is mediated via inhibition of vascular endothelial growth factor-2 (VEGFR2). The cytotoxic effect is mediated by tubulin inhibition. For example, Compound 1 of FIG. 1 overcomes two clinically important tumor resistance mechanisms that limit the activity of microtubule targeting agents: expression of P-glycoprotein and βIII tubulin. Compound 1 of FIG. 1 caused cellular microtubule depolymerization, arrested cells in the $G_2/M$ phase and triggered apoptotic cell death. In vivo, this compound reduced tumor size and vascularity in two flank xenograft models [the BLBC MDA-MB-435 and U251 glioma models] and in a 4T1 triple negative breast orthotopic allograft model. In these in vivo models, the activity of Compound 1 of FIG. 1 was superior to those of temozolomide (U251), docetaxel and sunitinib (MDA-MB-435 and 4T1) without overt toxicity to the animals.

The complexity of the angiogenic pathways implies that disrupting only a single aspect of angiogenesis may not result in significant clinical success. Multiple receptor tyrosine kinases (RTKs) are co-activated in tumors and redundant inputs drive and maintain downstream signaling, thereby limiting the efficacy of therapies targeting single RTKs. Resistance to VEGFR2 inhibition is associated with increased platelet-derived growth factor receptor-β (PDGFRβ) expression in tumor endothelial cells, increased recruitment of pericytes to tumor vasculature, and increases in other proangiogenic factors. Similarly epidermal growth factor receptor (EGFR) inhibition can lead to VEGFR2 up-regulation which subsequently promotes tumor growth signaling independent of EGFR and thus contributes to the resistance of EGFR inhibitors. The effect of EGFR inhibition can also be partially overcome by activation of PDGFR. Hence, targeting multiple RTKs maximizes the proportion of angiogenic signalling that is effectively targeted.

This invention discloses antiangiogenic agents which inhibit multiple RTKs such as VEGFR2, PDGFRβ, and EGFR among several others. Hence, it was of interest to explore the effect of structural changes on activity against the RTKs VEGFR2, PDGFRβ and EGFR in addition to having cytotoxic antitubulin effects with the goal of identifying single agents with antitubulin and multiple RTK inhibitory potential. Compounds 2-5 of FIG. 1 of this invention were designed as conformationally restricted analogs of Compound 1 of FIG. 1 of this invention.

Biological Evaluation

Antitubulin and RTK-Inhibitory Effects (Table 1)

Compounds 2, 4 and 5 of FIG. 1 of this invention are effective and potent inhibitors of bovine tubulin assembly comparable with combretastatin A-4.

Compounds 2-5 of FIG. 1 were evaluated for their activity against RTKs which are overexpressed by tumor endothelial cells. Compounds 2-5 of FIG. 1 have potencies comparable with sunitinib and semaxinib against VEGFR2 (Table 1). Compounds 3-5 of FIG. 1 have potencies comparable with erlotinib against EGFR. Compounds 3 and 4 of FIG. 1 have potencies comparable with DMBI against PDGFRβ.

Compounds 3-4 of FIG. 1 show potent inhibition of A431 cells and show activity comparable to that of doxorubicin.

While paclitaxel and docetaxel are 3-fold less potent in βIII-tubulin overexpressing cell line than in the wild type HeLe cells, compounds 2-5 of FIG. 1 inhibited both cell lines with equal potency independent of overexpression of βIII-tubulin.

TABLE 1

Inhibition of tubulin, colchicine binding and RTKs

| FIG. 1: compound | inhibition of tubulin assembly IC$_{50}$ (μM) | inhibition of colchicine binding (5 μM inhibitor) | inhibition of colchicine binding (1 μM inhibitor) | kinase inhibition IC$_{50}$ [whole-cell assays] VEGFR2 (nM) | PDGFR β (nM) | EGFR (nM) | A431 cytotoxicity (nM) | HeLa cytotoxicity Wild type (nM) | HeLa cytotoxicity βIII overexpressing (nM) |
|---|---|---|---|---|---|---|---|---|---|
| 2 | 3.3 ± 0.3 | | | 38.7 ± 7.1 | 90.3 ± 18.3 | 33.6 ± 5.6 | 40.1 ± 5.6 | 250 ± 0 | 250 ± 0 |
| 3 | >20 (no act) | | | 26.7 ± 4.6 | 7.2 ± 0.9 | 2.6 ± 0.42 | 2.3 ± 0.3 | 5000 ± 0 | 5000 ± 0 |
| 4 | 0.48 ± 0.008 | 92 ± 0.2 | 73 ± 3 | 33.0 ± 5.0 | 10.3 ± 1.7 | 2.3 ± 0.3 | 1.2 ± 0.07 | 14 ± 2 | 14 ± 1 |
| 5 | 0.91 ± 0.03 | 72 ± 2 | | 32.9 ± 4.9 | 30.2 ± 7.2 | 4.9 ± 0.6 | 8.1 ± 0.8 | 60 ± 0 | 58 ± 2 |
| combretastatin A-4 | 1.2 ± 0.01 | 98 ± 0.3 | | | | | | 1.8 ± 0.4 | 2.5 ± 0.7 |
| paclitaxel | | | | | | | | 5.3 ± 2 | 16.1 ± 1 |
| docetaxel | | | | | | | | 4.0 ± 2 | 13 ± 4 |
| semaxinib | | | | 12.9 | | | | | |
| sunitinib | | | | 18.9 ± 2.7 | 83.1 ± 10.1 | 172.1 ± 19.4 | | | |
| erlotinib | | | | 124.7 ± 18.2 | 12.2 ± 1.9 | 1.2 ± 0.2 | | | |
| DMBI | | | | | | 3.75 | | | |
| doxorubicin | | | | | | | 1.35 ± 0.03 | | |

Effect on [$^3$H]colchicine binding (Table 1)

Compounds 4 and 5 shown in FIG. 1 were potent inhibitors (activity comparable with that of combretastatin A-4) of bovine brain tubulin assembly and of [$^3$H]colchicine binding to tubulin, indicating that these compounds bind at the colchicine site on tubulin.

TABLE 2

Tumor cell inhibitory activity (NCI) GI$_{50}$ ($10^{-8}$M) of Compounds 2 and 4 of FIG. 1

| Panel/ Cell line | GI$_{50}$ ($10^{-8}$M) Compound 2 | GI$_{50}$ ($10^{-8}$M) Compound 4 | Panel/ Cell line Colon | GI$_{50}$ ($10^{-8}$M) Compound 2 | GI$_{50}$ ($10^{-8}$M) Compound 4 | Panel/ Cell line | GI$_{50}$ ($10^{-8}$M) Compound 2 | GI$_{50}$ ($10^{-8}$M) Compound 4 | Panel/ Cell line Renal | GI$_{50}$ ($10^{-8}$M) Compound 2 | GI$_{50}$ ($10^{-8}$M) Compound 4 |
|---|---|---|---|---|---|---|---|---|---|---|---|
| Leukemia | | | Cancer | | | Melanoma | | | Cancer | | |
| CCRF-CEM | 22.6 | 3.35 | COLO 205 | 23.2 | 2.63 | LOX IMVI | 52.1 | 5.88 | 786-0 | 93.4 | 9.32 |
| HL-60(TB) | 22.2 | 2.68 | HCC-2998 | 31.8 | 7.11 | MALME-3M | 33.0 | 1.77 | A498 | 19.7 | 2.02 |
| K-562 | 11.1 | 3.37 | HCT-116 | 36.8 | 3.50 | M14 | 25.2 | 2.95 | ACHN | 83.0 | 17.2 |
| MOLT-4 | 34.5 | 5.08 | HCT-15 | 36.6 | 3.81 | MDA-MB-435 | 34.1 | 2.14 | CAKI-1 | 34.1 | 5.66 |
| RPMI-8226 | 26.6 | 3.69 | HT29 | | 3.51 | SK-MEL-2 | | 2.86 | RXF 393 | 21.2 | 2.54 |
| SR | 92.2 | 3.38 | KM12 | 36.6 | 4.45 | SK-MEL-28 | 36.8 | 4.87 | SN12C | 61.8 | 8.87 |
| NSCLC | | | SW-620 | 37.0 | 3.84 | SK-MEL-5 | 32.5 | 5.42 | TK10 | 12.3 | |
| A549/ATCC | 40.6 | 4.40 | CNS Cancer | | | UACC-257 | 10.8 | 7.82 | UO-31 | 39.0 | 20.9 |
| EKVX | 46.3 | | SF-268 | 72.3 | 35.0 | UACC-62 | 65.9 | 47.5 | Prostate Cancer | | |
| HOP-62 | 37.9 | 4.78 | SF-295 | 19.2 | 3.04 | Ovarian cancer | | | PC-3 | | 4.96 |
| HOP-92 | 18.9 | 4.71 | SF-539 | 26.0 | 2.54 | IGROVI | 44.0 | 9.58 | DU-145 | 38.3 | 4.44 |
| NCI-H226 | 13.6 | 30.4 | SNB-19 | 54.9 | 5.47 | OVCAR-3 | 28.5 | 3.52 | Breast Cancer | | |
| NCI-H23 | 32.0 | 4.58 | SNB-75 | 18.2 | 2.78 | OVCAR-4 | 46.8 | | MCF7 | 24.8 | 3.33 |
| NCI-H322M | 36.2 | 7.36 | U251 | 31.6 | 4.43 | OVCAR-5 | 54.3 | 26.9 | MDA-MB-231/ATCC | 64.1 | 6.37 |
| NCI-H460 | 33.7 | 3.87 | | | | OVCAR-8 | 48.7 | 4.91 | HS 578T | 58.2 | 6.23 |

TABLE 2-continued

Tumor cell inhibitory activity (NCI) GI$_{50}$ (10$^{-8}$M) of Compounds 2 and 4 of FIG. 1

| Panel/ Cell line | GI$_{50}$ (10$^{-8}$M) Compound | | Panel/ Cell line Colon | GI$_{50}$ (10$^{-8}$M) Compound | | Panel/ Cell line | GI$_{50}$ (10$^{-8}$M) Compound | | Panel/ Cell line Renal | GI$_{50}$ (10$^{-8}$M) Compound | |
|---|---|---|---|---|---|---|---|---|---|---|---|
| Leukemia | 2 | 4 | Cancer | 2 | 4 | Melanoma | 2 | 4 | Cancer | 2 | 4 |
| NCI-H522 | 31.6 | 2.39 | | | | NCI/ADR-RES | 26.5 | 3.28 | BT-549 | 75.5 | 4.82 |
| | | | | | | SK-OV-3 | 42.3 | 4.54 | T-47D | 12.8 | |
| | | | | | | | | | MDA-MB-468 | 15.3 | 3.01 |

NCI 60 Tumor Panel (Table 2)

Compounds 2 (a tubulin and VEGFR2 inhibitor) and 4 (a tubulin, VEGFR2, EGFR and PDGFRβ inhibitor) shown in FIG. 1 were evaluated for tumor cytotoxicity in the NCI 60 tumor cell line panel. Both compounds show 2- to 3-digit nanomolar GI$_{50}$.

CAM Assay

Compound 4 shown in FIG. 1 was tested for its effects on blood vessel formation in the chicken chorioallantoic membrane (CAM) antiangiogenic activity assay and was found to have an IC$_{50}$ value of 2.2±0.4 µM [sunitinib, IC$_{50}$=1.3±0.07 µM; erlotinib IC$_{50}$=29.1±1.9 µM]

In Vivo Studies

While not being bound to any particular theory on mechanism of action, we believe that Compound 4 shown in FIG. 1 has four separate mechanisms of action in a single entity including inhibition of tubulin, PDGFRβ, VEGFR2 and EGFR. Compound 4 shown in FIG. 1 was evaluated in preclinical tumor models in mice.

4T1-Luc2GFP Triple Negative Mouse Breast Cancer Model

BALB/c mice were implanted with 7.5 k 4T1-Luc2GFP triple negative mouse breast cancer cells orthotopically into mammary fat pad 4. 7 days after implantation, tumors are visible in over 90% of animals. At day 8 and continuing twice weekly until the experiment end, the MTD of compound 4-HCl (i.e. the hydrochloride salt of compound 4 shown in FIG. 1), determined to be 40 mg/kg, was given IP to tumor-bearing mice; doxorubicin at its MTD of 1 mg/kg weekly was given as a comparison; Both drugs were in solvent (5% solutol-15, 5% PharmaSolve in normal saline) and a solvent control group was included in addition to sham injected (untreated) group. Primary tumor volume and animal weights was assessed by calipers throughout the experiment.

Figure 2:
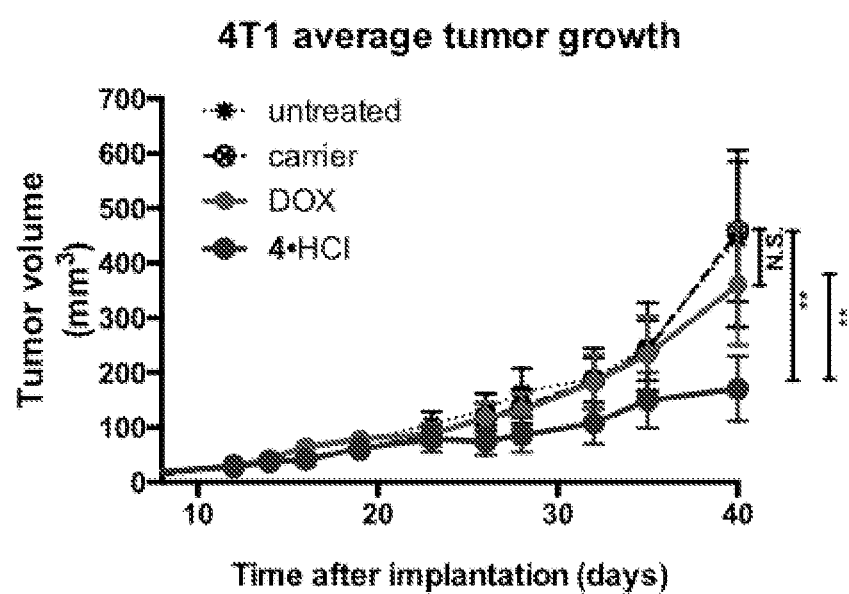
FIG. 2 shows the effect of the HCl salt form of Compound 4 of this invention (chemical structure of Compound 4 shown in FIG. 1) upon triple negative mouse tumors.

FIG. 2 shows the effect of Compound 4-HCl (HCl salt form of Compound 4 shown in FIG. 1) on triple negative mouse breast tumors. In FIG. 2, Compound 4-HCl (i.e. the salt form of Compound 4 shown in FIG. 4, here as the hydrochloride salt form) significantly reduced 4T1 primary growth vs carrier or vs doxorubicin.

Figure 3:
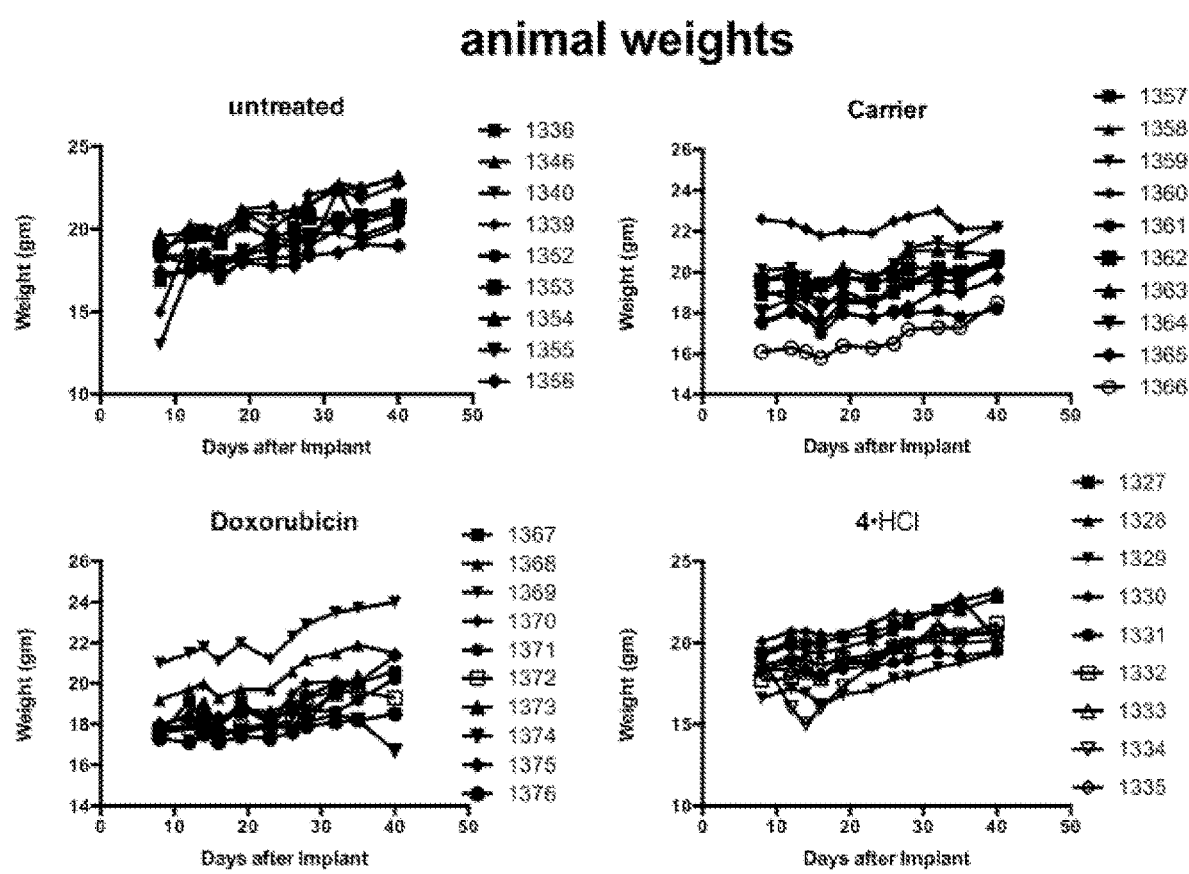
FIG. 3 shows the effect of the HCl salt form of Compound 4 of this invention (chemical structure of Compound 4 shown in FIG. 1) upon animal weight.

FIG. 3 shows the effect of Compound 4 shown in FIG. 1 (here as the HCl salt form) on animal weight. Doxorubicin began to result in weight loss in a few animals. However, Compound 4-HCl resulted in no change in animal weight (animals gained weight, FIG. 4), indicating lower systemic toxicity.

Figure 4:
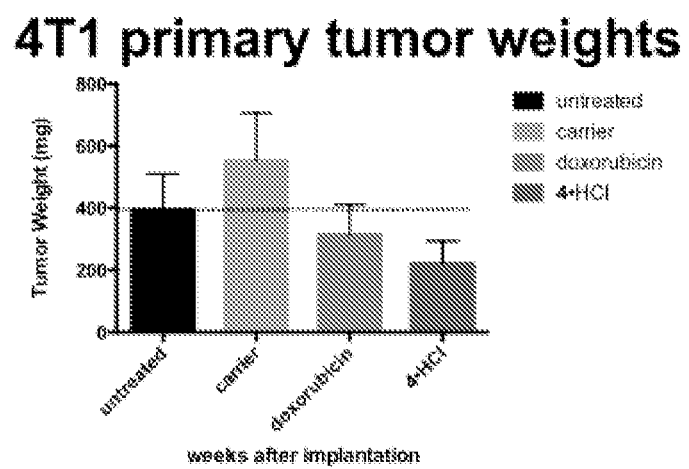
FIG. 4 shows the effect of the HCl salt form of Compound 4 of this invention (chemical structure of Compound 4 shown in FIG. 1) on tumor weight.

On day 40, all animals were injected IV with fluorescently labeled dextran as a marker of vasculature. Tumors were excised and weighed; lungs were excised and evaluated for metastases. Small micro metastases (1-9 cells without any vasculature); large micro metastases (>10 cells with no vasculature) and macrometastases (>10 cells with apparent vasculature) were counted. FIG. 4 shows the effect of Compound 4 of FIG. 4 (here as the HCl salt) on tumor weight.

FIG. 4 shows the effect of the HCl salt form of Compound 4 of FIG. 1 on animal weight. Compound 4-HCl reduced tumor weight at the end of the experiment.

Figure 5:
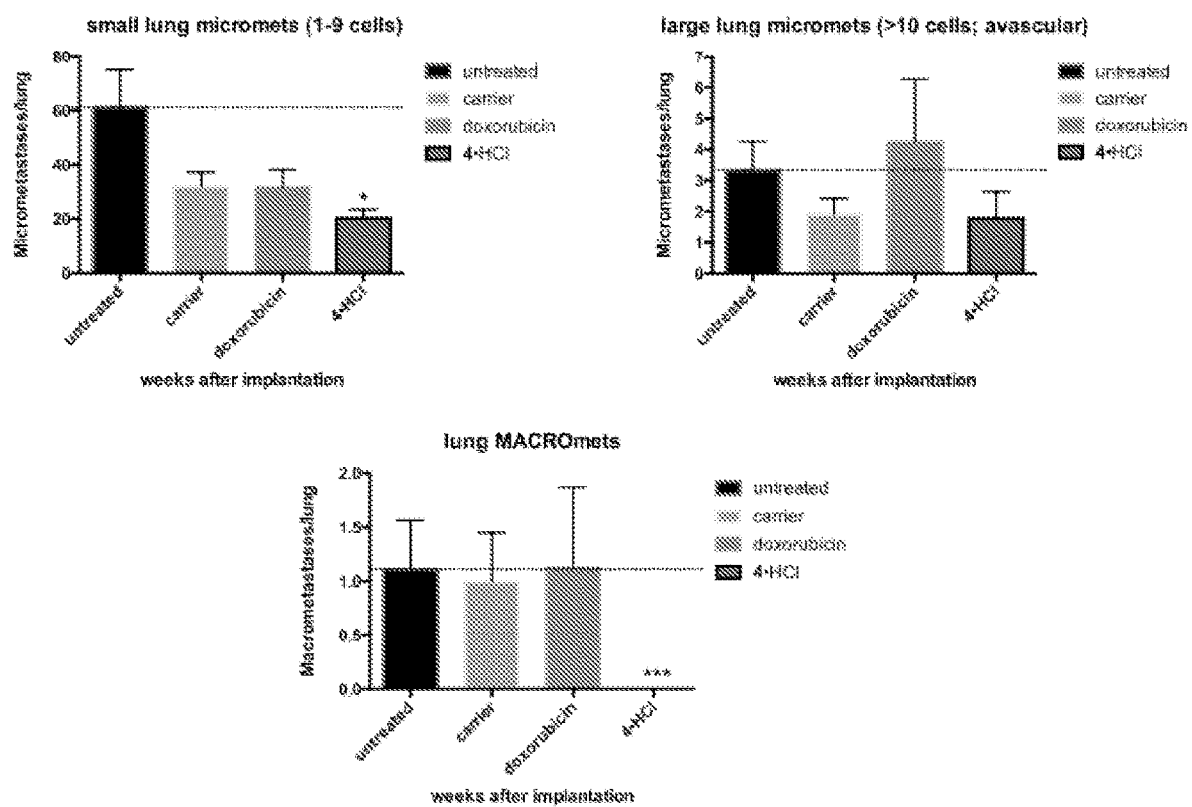
FIG. 5 shows the effect of the HCl form of Compound 4 of this invention (chemical structure of Compound 4 shown in FIG. 1) upon lung micrometastases and macrometastases.

FIG. 5 shows the effect of Compound 4 of FIG. 1 (here as the HCl salt form) on lung micro- and macrometastases. Compound 4-HCl reduced the number of lung small micro metastases and more importantly, in the 4-HCl compound treated animals none had any lung macrometastases.

In summary, we discovered that these conformationally restricted analogs of Compound 1 of FIG. 1 had improved activities against PDGFRβ and EGFR in addition to having tubulin and VEGFR2 inhibitory activities. We believe that in addition to delaying or preventing tumor cell resistance these water-soluble compounds with antiangiogenic effects via multiple RTK inhibition and cytotoxic effects via tubulin inhibition in single entities could perhaps circumvent pharmacokinetic problems of multiple agents, avoid drug-drug interactions, be used at lower doses to alleviate toxicity and be devoid of overlapping toxicities.

CHEMISTRY- SYNTHESIS SCHEME (GENERAL)

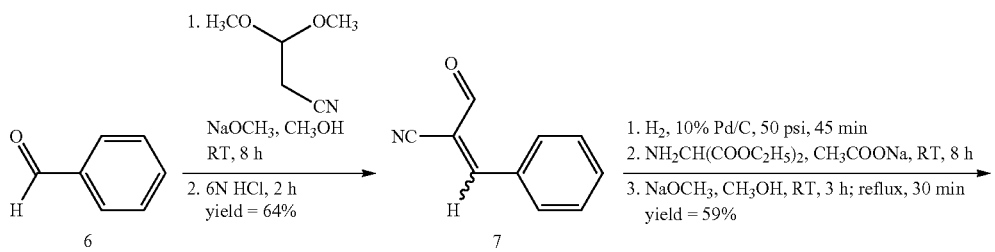

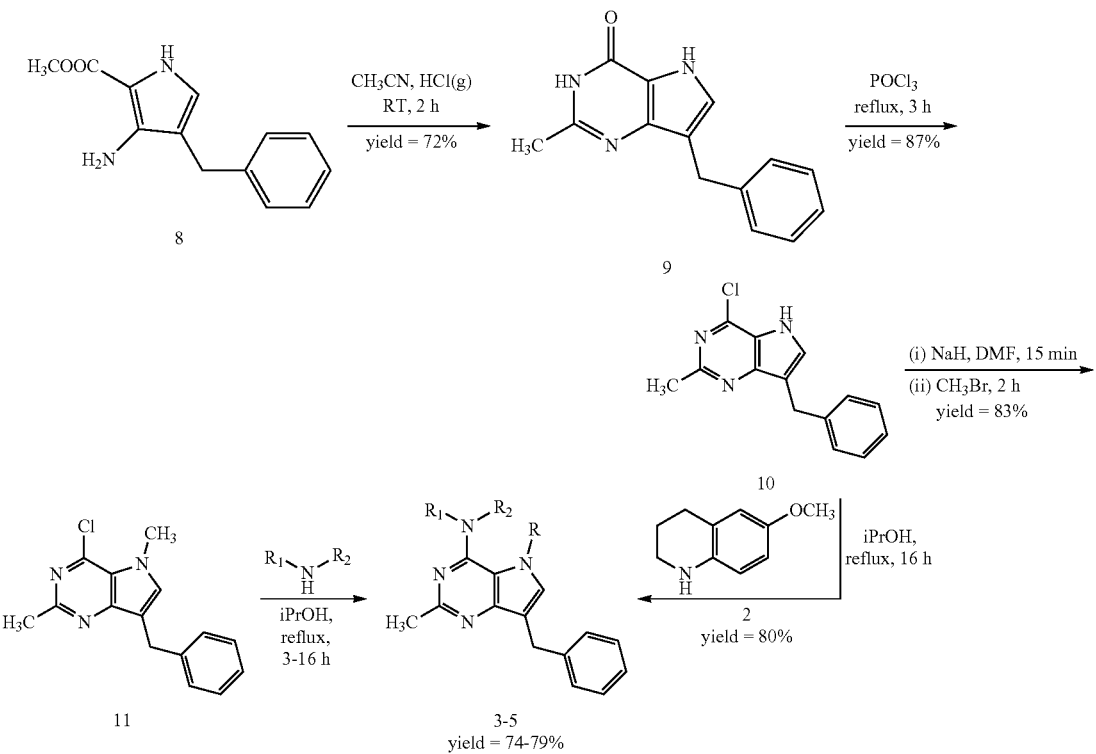
CHEMISTRY - SYNTHESIS SCHEMES
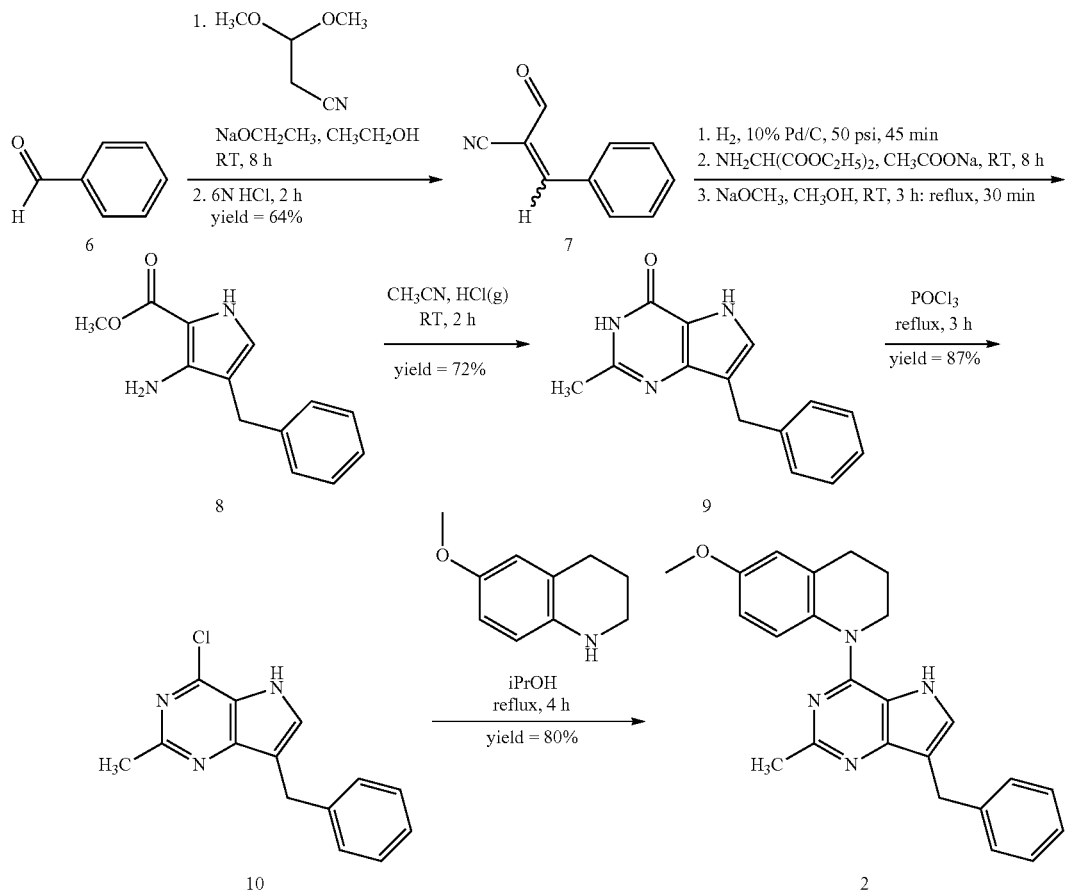

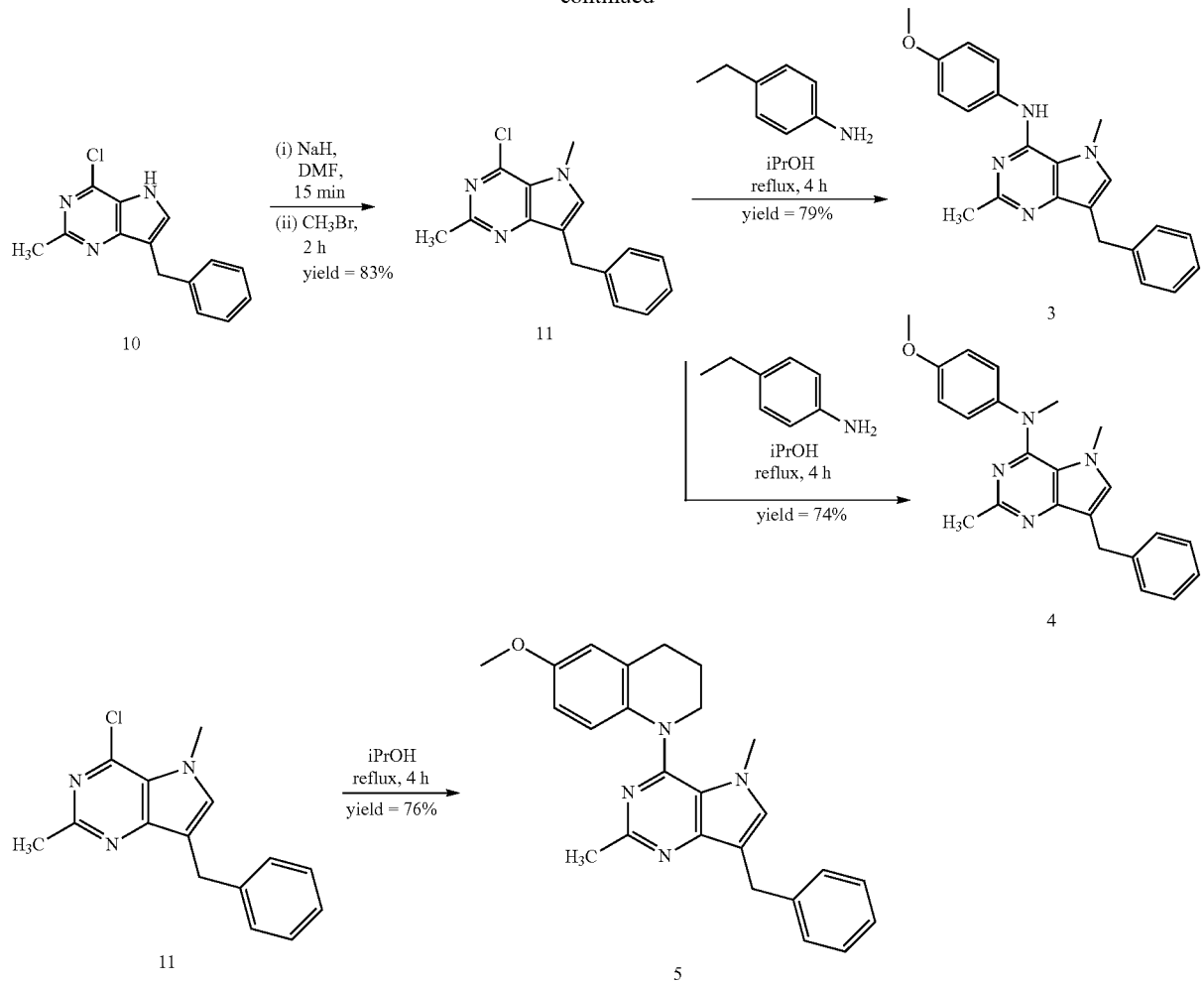

EXPERIMENTAL

All evaporations were carried out in vacuum with a rotary evaporator. Analytical samples were dried in vacuo in a CHEM-DRY drying apparatus over $P_2O_5$ at 50° C. Melting points were determined either using a MEL-TEMP II melting point apparatus with FLUKE 51 K/J electronic thermometer or using an MPA100 OptiMelt automated melting point system and are uncorrected. Nuclear magnetic resonance spectra for proton ($^1$H NMR) were recorded on the Bruker Avanice II 400 (400 MHz) or Bruker Avanice II 500 (500 MHz) NMR systems with TopSpin processing software. The chemical shift values (δ) are expressed in ppm (parts per million) relative to tetramethylsilane as an internal standard: s, singlet; d, doublet; dd, doublet of doublet; t, triplet; q, quartet; m, multiplet; br, broad singlet; td, triplet of doublet; dt, doublet of triplet; quin, quintet. Thin-layer chromatography (TLC) was performed on Whatman® PE SIL G/UV254 flexible silica gel plates and the spots were visualized under 254 and 365 nm ultraviolet illumination. Proportions of solvents used for TLC are by volume. All analytical samples were homogeneous on TLC in at least two different solvent systems. Column chromatography was performed on the silica gel (70 to 230 meshes, Fisher Scientific) column. Flash chromatography was carried out on the CombiFlash® Rf systems, model COMBIFLASH RF. Pre-packed RediSep® Rf normal-phase flash columns (230 to 400 meshes) of various sizes were used. The amount (weight) of silica gel for column chromatography was in the range of 50-100 times the amount (weight) of the crude compounds being separated. Elemental analyses were performed by Atlantic Microlab, Inc., Norcross, Ga. Element compositions are within 0.4% of the calculated values. Fractional moles of water or organic solvents frequently found in some analytical samples could not be prevented despite 24 to 48 hours of drying in vacuo and were confirmed where possible by their presence in the $^1$H NMR spectra.

Methyl 3-amino-4-benzyl-1H-pyrrole-2-carboxylate (8)

Benzaldehyde (6, 20 g, 0.25 mol) and 3,3-dimethoxypropionitrile (35 g, 0.30 mol) were mixed together and added to a solution of sodium ethoxide in ethanol (0.5 M) during 15 min. The mixture was stirred at room temperature for 8 hours. Most of the solvent was removed in vacuo, and the residue was partitioned between EtOAc (500 mL) and water (450 mL). The organic layer was separated, washed with brine, dried with sodium sulphate and the solvent evaporated in vacuo. The residual oil was treated cautiously with 6 N HCl (75 mL), and the mixture was stirred at room temperature for 2 hours. The solid was filtered off, washed well with water, and dried in vacuuo to give an off-white powder (7) which was shaken with methanol and 10% Pd/C under 50 psi $H_2$ in a hydrogenation bottle for 45 min. The catalyst was removed by filtration, a mixture of diethyl aminomalonate, sodium acetate, and water was added, and the mixture was stirred at room temperature for 8 hours. Most of the solvent was removed in vacuo, and the residue was partitioned between EtOAc and water. The organic layer was separated and dried over sodium sulphate and evaporated in vacuo. The residual yellow oil was dissolved in methanol containing sodium methoxide, stirred at room temperature for 3 hours and then heated to reflux for 30 minutes. Most of the solvent was evaporated in vacuo, and the residue was treated with water (200 mL) to give 8 as a light yellow solid which was flash chromatographed with 1% (v/v) $CH_3OH$ in $CHCl_3$. mp: 120-122° C.; $^1$H NMR (400 MHz, DMSO-$d_6$) □ ppm 3.62 (s, 2H, $CH_2$) 3.68 (s, 3H, $CH_3$) 4.84 (br, 2H, exch, $NH_2$) 6.46 (d, J=3.51 Hz, 1H, 6-H) 7.11-7.16 (m, 1H, $C_6H_5$) 7.19-7.27 (m, 4H, $C_6H_5$) 10.47 (br, 1H, exch, NIH).

7-Benzyl-2-methyl-3H-pyrrolo[3,2-d]pyrimidin-4 (5H)-one [9]

To a 250 mL flask was added 8 (1.5 g, 6.51 mmol) and acetonitrile (30 mL). Dry HCl gas was bubbled through the solution at room temperature for 15 min. A precipitate was formed, and it dissolved as the reaction progressed. HCl gas was bubbled through the solution for an additional hour, and the mixture was stirred for 2 h. Most of the solvent was evaporated in vacuo, water (20 mL) was added, and the aqueous mixture was neutralized with ammonia to afford a precipitate that was removed by filtration, washed with water and dried in vacuo to afford a light yellow solid. Silica gel and methanol were added; the solvent was evaporated to afford a plug. The silica gel plug obtained was loaded onto a silica gel column and eluted with 1% (v/v) $MeOH/CHCl_3$. Fractions containing the product (TLC) were pooled, and the solvent was evaporated to afford 9 (1.12 g, 72%). TLC $R_f$=0.42 ($CH_3OH:CHCl_3$; 1:20); white solid; mp, 254-256° C.; $^1$H NMR, DMSO-$d_6$: δ 2.29 (s, 3H, 2-$CH_3$) 3.90 (s, 2H, $CH_2$) 7.07 (d, J=2.90 Hz, 1H, Ar) 7.10-7.15, (m, 1H, Ar) 7.21-7.24, (m, 4H, Ar) 12.086 (s, 1H, exch, NH) Anal. Calcd. for $C_{14}H_{13}N_3O.0.1H_2O$: C, 69.75; H, 5.52; N, 17.43. Found C, 69.81; H, 5.52; N, 17.44.

7-Benzyl-4-chloro-2-methyl-5H-pyrrolo[3,2-d]pyrimidine [10]

Compound 9 (1.5 g, 6.27 mmol) was added to $POCl_3$ (12 mL) and heated at reflux for 3 h. The solvent was evaporated in vacuo, and the residue was adjusted to pH 8 with an ammonia solution. The resulting precipitate was removed by filtration, washed with water and dried in vacuo over $P_2O_5$ to afford a light yellow solid. Silica gel (4.5 g) and methanol (20 mL) were added; the solvent was evaporated to afford a plug. The silica gel plug obtained was loaded onto a silica gel column and eluted with 1% (v/v) $CH_3OH/CHCl_3$. Fractions containing the product (TLC) were pooled, and the solvent was evaporated to afford 10 (1.41 g, 87%). TLC $R_f$=0.56 ($CH_3OH:CHCl_3$; 1:20); white solid; mp 181-183° C.; $^1$H NMR, DMSO-$d_6$: δ 2.61 (s, 3H, 2-$CH_3$) 4.04 (s, 2H, $CH_2$) 7.13-7.28 (m, 5H, Ar) 7.68 (d, J=2.72 Hz, 1H, CH) 12.086 (s, 1H, exch, 5-NH) Anal. Calcd. for $C_{14}H_{12}N_3Cl$: C, 65.25; H, 4.69; N, 16.30. Found C, 65.23; H, 4.70; N, 16.31.

1-(7-Benzyl-2-methyl-5H-pyrrolo[3,2-d]pyrimidin-4-yl)-6-methoxy-1,2,3,4-tetrahydroquinoline (2)

Compound 10 (0.1 g, 0.38 mmol) and 6-methoxy-1,2,3,4-tetrahydroquinoline (0.07 g, 1.05 mmol) were dissolved in isopropanol (20 mL) and heated at reflux for 4 h. The solvent was evaporated in vacuo, and the residue was purified by column chromatography ($CHCl_3:CH_3OH$; 50:1; v/v) to give a brown solid (120.0 mg): yield=80%; TLC $R_f$=0.6 ($CH_3OH:CHCl_3$; 1:25). pale yellow solid; mp 262-264° C.; $^1$H NMR (400 MHz, DMSO-$d_6$) □ ppm 1.97-2.05 (m, 2H, $CH_2$) 2.67 (s, 3H, $CH_3$) 2.76-2.82 (m, 2H, $CH_2$) 3.79 (s, 3H, $CH_3$) 4.11 (s, 4H, $CH_2$) 6.77-6.82 (m, 1H, Ar) 6.92-6.96 (m, 1H, Ar) 7.12-7.24 (m, 2H, Ar) 7.28-7.34 (m, 4H, Ar) 7.44-7.48 (m, 1H, Ar) 10.88 (s, 1H, exch, NH) 14.36 (s, 1H, exch, HCl) Anal. Calcd. for $C_{24}H_{24}N_4O.HCl.0.25H_2O$: C, 67.75; H, 6.04; N, 13.17; Cl, 8.33. Found C, 67.84; H, 6.21; N, 12.95; Cl, 8.06.

7-Benzyl-4-chloro-2,5-dimethyl-5H-pyrrolo[3,2-d] pyrimidine (11)

Compound 10 (300 mg, 1.16 mmol) was dissolved in dimethylformamide (20 mL) and sodium hydride (31 mg, 1.28 mmol) was added under nitrogen. The mixture was allowed to stir for 15 minutes after no further production of hydrogen gas was observed. Methyl bromide (0.2 mL) was added and the reaction was stirred for 2 hours. The reaction was quenched by addition of water and ethylacetate was added. The organic layer was collected, washed with brine and dried over sodium sulphate. A silica gel plug was made and purified by column chromatography ($CHCl_3$:
MeOH; 100:1 v/v) to give an off-white solid yield=83%; TLC $R_f$=0.5 ($CH_3OH:CHCl_3$; 1:25). white solid; mp, 145-147° C. $^1$H NMR (400 MHz, DMSO-$d_6$) □ ppm 2.62 (s, 3H, $CH_3$) 4.01 (s, 3H, $CH_3$) 4.03 (s, 2H, $CH_2$) 7.17 (td, J=5.65, 2.76 Hz, 1H, 6-CH) 7.26-7.30 (m, 4H, $C_6H_5$) 7.64 (s, 1H, $C_6H_5$).

7-Benzyl-N-(4-methoxyphenyl)-2,5-dimethyl-5H-pyrrolo[3,2-d]pyrimidin-4-amine (3)

Compound 3 (synthesized from 11 and p-anisidine as described for 2): yield=79%; TLC $R_f$=0.5 ($CH_3OH:CHCl_3$; 1:20). white solid; mp, 291-292° C.; $^1$H NMR (DMSO-$d_6$): δ 2.66 (s, 3H, 2-$CH_3$) 3.6 (s, 3H, $NCH_3$) 3.82 (s, 3H, $OCH_3$) 4.08 (s, 2H, $CH_2$) 7.08 (d, 2H, J=8.84 Hz, Ar) 7.17-7.26 (m, 6H, Ar and 6-CH) 7.4 (d, 2H, J=8.73, Ar) 9.41 (br, 1H, exch, NH) 14.43 (s, 1H, exch, HCl). Anal. Calcd. for $C_{22}H_{22}N_4O.HCl$: C, 66.91; H, 5.87; N, 14.19; Cl, 8.98. Found C, 66.88; H, 5.86; N, 14.07; Cl, 8.84.

7-Benzyl-N-(4-methoxyphenyl)-N,2,5-trimethyl-5H-pyrrolo[3,2-d]pyrimidin-4-amine (4)

Compound 4 (synthesized from 11 and 4-methoxy N-methyl aniline as described for 2): yield=74%; TLC $R_f$=0.5 ($CH_3OH:CHCl_3$; 1:20). grey solid; mp, 186-187° C.; $^1$H NMR (400 MHz, DMSO-$d_6$) □ ppm 2.73 (s, 3H, $CH_3$) 2.80 (s, 3H, $CH_3$) 3.63 (s, 3H, $CH_3$) 3.78 (s, 3H, $CH_3$) 4.08 (s, 2H, $CH_2$) 7.00 (d, J=9.03 Hz, 2H, Ar) 7.22 (d, J=5.52 Hz, 1H, Ar) 7.25-7.33 (m, 6H, Ar) 7.37 (s, 1H, Ar) 8.33 (s, 1H, Ar) 14.63 (s, 1H, exch, HCl) Anal. Calcd. for $C_{23}H_{24}N_4O.HCl$: C, 67.55; H, 6.16; N, 13.70; Cl, 8.67. Found C, 67.41; H, 6.20; N, 13.59; Cl, 8.61.

1-(7-Benzyl-2,5-dimethyl-5H-pyrrolo[3,2-d]pyrimidin-4-yl)-6-methoxy-1,2,3,4-tetrahydroquinoline (5)

Compound 5 (synthesized from 11 and 6-methoxy-1,2,3,4-tetrahydroquinoline as described for 2): yield=76%; TLC $R_f$ 0.6 ($CH_3OH:CHCl_3$; 1:20) white solid; mp, 130-132° C.; $^1H$ NMR (400 MHz, DMSO-$d_6$) ☐ ppm 2.07 (t, J=6.53 Hz, 2H, $CH_2$) 2.72 (s, 3H, $CH_3$) 2.79-2.88 (m, 2H, $CH_2$) 2.97 (s, 3H, $CH_3$) 3.72-3.78 (m, 3H, $CH_3$) 3.96-4.06 (m, 2H, $CH_2$) 4.13 (s, 2H, $CH_2$) 6.68-6.72 (m, 1H, Ar) 6.79 (d, J=9.03 Hz, 1H, Ar) 6.91 (d, J=2.76 Hz, 1H, Ar) 7.22 (td, J=5.84, 2.64 Hz, 1H, Ar) 7.30-7.35 (m, 4H, Ar) 7.50 (s, 1H, Ar) 14.71 (s, 1H, exch, HCl).

REFERENCES

1. Gangjee, A.; Pavana, R. K.; Ihnat, M. A.; Thorpe, J. E.; Disch, B. C.; Bastian, A.; Bailey-Downs, L. C.; Hamel, E.; Bai, R. Discovery of antitubulin agents with antiangiogenic activity as single entities with multitarget chemotherapy potential. *ACS. Med. Chem. Lett,* 2014, doi: 10.1021/ml14004793
2. Gangjee, A.; Zaware, N.; Raghavan, S.; Disch, B. C.; Thorpe, J. E.; Bastian, A.; Ihnat, M. A. Synthesis and biological activity of 5-chloro-N4-substituted phenyl-9H-pyrimido[4,5-b]indole-2,4-diamines as vascular endothelial growth factor receptor-2 inhibitors and antiangiogenic agents. *Bioorg. Med. Chem.* 2013, 21, 1857-1864.
3. Gangjee, A.; Kurup, S.; Ihnat, M. A.; Thorpe, J. E.; Disch, B. C. $N^4$-aryl-6-substituted-phenylmethyl-7H-pyrrolo[2,3-d]pyrimidine-2,4-diamines as receptor tyrosine kinase inhibitors. *Bioorg. Med. Chem.* 2012, 20, 910-914.
4. Gangjee, A.; Zaware, N.; Raghavan, S.; Ihnat, M.; Shenoy, S.; Kisliuk, R. L. Single agents with designed combination chemotherapy potential: Synthesis and evaluation of substituted pyrimido[4,5-b]indoles as receptor tyrosine kinase and thymidylate synthase inhibitors and as antitumor agents. *J. Med. Chem.* 2010, 53, 1563-1578.

What is claimed is:

1. A compound that is 7-Benzyl-4-chloro-2, 5-dimethyl-5H-pyrrolo[3,2-d]pyrimidine, or a pharmaceutically acceptable salt thereof.

2. A method of treating a patient diagnosed with cancer comprising administering to the patient a therapeutically effective amount of a compound of the following formula:

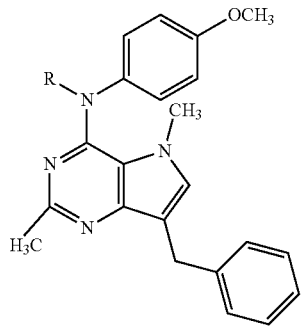

or a pharmaceutically acceptable salt thereof, wherein R is a straight or branched chain alkyl group having from 1 to 10 carbon atoms, wherein the alkyl group is partially or completely saturated, for treating cancer.

3. A method of treating a patient diagnosed with cancer comprising administering to the patient a therapeutically effective amount of a compound selected from the group of 7-Benzyl-4-chloro-2,5-dimethyl-5H-pyrrolo[3,2-d]pyrimidine, and 7-Benzyl-N-(4-methoxyphenyl)-N, 2, 5-trimethyl-5H-pyrrolo[3,2-d]pyrimidin-4-amine, or a pharmaceutically acceptable salt thereof, for treating cancer.

* * * * *